United States Patent [19]

Sun et al.

[11] Patent Number: 5,196,619
[45] Date of Patent: Mar. 23, 1993

[54] INHIBITING POPCORN POLYMER FORMATION WITH SULFUR-CONTAINING COMPOUNDS

[76] Inventors: Hsiang-ning Sun, 4212 Villanova, Houston, Tex. 77005; John J. Cikut, 3700 Kingwood Dr. Apt. 1306, Kingwood, Tex. 77339; Roque V. Martir, 2214 Enchanted Isle Dr., Houston, Tex. 77062; Jos P. Wristers, 16011 Craighurst, Houston, Tex. 77059

[21] Appl. No.: 647,356

[22] Filed: Jan. 29, 1991

[51] Int. Cl.$^5$ ............................................. C07C 7/20
[52] U.S. Cl. .................................. 585/002; 585/3; 585/950; 208/48 AA
[58] Field of Search ...................... 585/2, 3, 950; 134/22.19; 208/48 AA; 203/8

[56] References Cited

U.S. PATENT DOCUMENTS

| | | |
|---|---|---|
| 2,947,795 | 8/1960 | Keown et al. . |
| 3,148,225 | 9/1964 | Albert et al. . |
| 3,175,012 | 3/1965 | Colbert . |
| 3,265,751 | 8/1966 | McCoy et al. . |
| 3,265,752 | 8/1966 | Whiton et al. . |
| 3,407,240 | 10/1968 | Sakashita et al. . |
| 3,476,656 | 11/1969 | van Tassell et al. ............... 585/950 |
| 3,493,603 | 2/1970 | Albert et al. . |
| 3,523,141 | 8/1970 | Sakashita et al. . |
| 3,531,540 | 9/1970 | Marshall et al. . |
| 3,560,577 | 2/1971 | Benjamin et al. . |
| 4,404,413 | 9/1983 | Haskell ................................ 585/2 |
| 4,417,084 | 11/1983 | Chu . |
| 4,504,594 | 3/1985 | Chu ................................. 585/445 |

FOREIGN PATENT DOCUMENTS

| | | |
|---|---|---|
| 0035329 | 9/1981 | European Pat. Off. . |
| 63-223003 | 9/1988 | Japan . |
| 1182159 | 2/1970 | United Kingdom . |

OTHER PUBLICATIONS

Liu, "Plugging-Up of Equipment by Self-Polymerization Butadiene Production and Its Prevention," China Synthetic Rubber Industry, 11(5) 357–360 (1988).

Liu et al., "Determination of Traces of Diethylhydroxylamine Inhibitor in C5 Fraction by Gas Chromatography," China Synthetic Rubber Industry, 12(6), 408–410 (1989).

Chemical Abstracts, vol. 1213, No. 22, issued Nov. 26, 1990 Columbus, Ohio, US, Abstract No. 192117Q Mitsubishi Petrochemical, "Polymerization inhibition of styrenes by nitrosophenols and mercaptans".

Chemical Abstracts, III: 78786r (Jan. 1989).

*Primary Examiner*—Anthony McFarlane

[57] ABSTRACT

Inhibition of popcorn polymer growth by treatment with a sulfur-containing compound. The sulfur-containing compound can be added to organic material from which popcorn polymer is formed, or applied to extant popcorn polymer.

16 Claims, No Drawings

INHIBITING POPCORN POLYMER FORMATION WITH SULFUR-CONTAINING COMPOUNDS

CONCURRENTLY FILED APPLICATIONS

Concurrently with this application, also filed were applications entitled METHOD FOR INHIBITING POPCORN POLYMER FORMATION BY HEAT, U.S. application Ser. No. 647,365, filed Jan. 29, 1991; INHIBITING POPCORN POLYMER FORMATION WITH COMPOUNDS INCORPORATING GROUP IV ELEMENTS, U.S. application Ser. No. 647,357, filed Jan. 29, 1991; INHIBITING POPCORN POLYMER FORMATION WITH ESTERS OF INORGANIC ACIDS, U.S. application Ser. No. 647,359, filed Jan. 29, 1991; and INHIBITING POPCORN POLYMER FORMATION WITH ALKYL HALIDES, U.S. application Ser. No. 647,358, filed Jan. 29, 1991. These applications are all incorporated herein in their entireties, by reference thereto.

BACKGROUND OF THE INVENTION

1. Field of the Invention

The present invention is directed to inhibiting popcorn polymer formation in organic material, and likewise to inhibiting further growth of popcorn polymer seeds or deposits already in existence. The desired result is effected by treatment of the organic material, or the seeds or deposits, with an amount of one or more mercaptans sufficient to inhibit popcorn polymer growth.

2. Description of Background and Other Information

Popcorn polymers are known to form from all manner of organic material, particularly olefinically unsaturated monomers, including olefins and diolefins; especially susceptible are the conjugated diolefins, e.g., butadiene and isoprene, and vinyl compounds, e.g., styrenes and acrylates. Known as popcorn polymers because they resemble popped corn, these polymers are also referred to in the art as sponge polymers, granular polymers, cauliflower-like polymers, nodular polymers, fluffy polymers, proliferous polymers, and crusty polymers.

Popcorn polymer has been considered to occur from spontaneous monomer polymerization. It can occur in both liquid phase and vapor phase, and at any stage of use or handling of the monomer, e.g., recovery, separation, manufacturing, purification, storage, etc. High concentrations of monomer are particularly advantageous for its formation.

Specifically, it appears that the presence of one or more initiators—e.g., water, oxygen, hydrogen, peroxide—results in the formation of popcorn polymer "seeds" in the organic material. The seeds themselves then perpetuate polymerization, without further requiring an initiator and/or a crosslinking agent; they serve as sites for further polymerization.

As the particular mechanism, it is believed that monomer diffuses through the surface of the growing polymer mass, and is added to the polymer at the center thereof. For this reason, such polymerization is referred to as occurring "from the inside out."

Consequently, there is continued incorporation of monomer into the polymer phase, leading to buildup of the popcorn polymer. The result is a hard polymeric foulant, which can cause serious equipment and safety concerns if left unchecked.

A particular problem attendant upon popcorn polymer formation is its extreme resistance to deactivation, once present in a system. Some of the seeds become attached to the processing and handling equipment, and cannot be readily removed by mechanical means; moreover, being insoluble in most common solvents, they are virtually impossible to wash out by use of such solvents.

Even after equipment and storage facilities have been cleaned thoroughly, residual particles of popcorn polymer remain, and promote unwanted polymer growth. Trace particles remaining in the equipment will stay active for long periods without the presence of monomer, and serve to initiate polymerization when once again contacted therewith.

Different inhibitors are known for use against popcorn polymer formation. Examples of these are the following: t-butylcatechol; sodium nitrite, as disclosed in LIU, "Plugging-Up of Equipment by Self-Polymerization Butadiene Production and Its Prevention," *China Synthetic Rubber Industry*, 11(5) 357–360 (1988); N,N-dialkylhydroxylamines, as disclosed in TOKAI ELECTRO-CHEMICAL CO., Japanese Kokai No. 66,223,003, as well as in LIU et al., "Determination of Traces of Diethylhydroxylamine Inhibitor in $C_5$ Fraction by Gas Chromatography," *China Synthetic Rubber Industry*, 12(6), 408–410 (1989), and in ALBERT, U.S. Pat. No. 3,148,225, the latter of these also referring to nitrites, nitroso compounds, $NO_2$, $N_2O_3$, phenolic compounds, sulfur, aromatic amines, and hydroxylamine as being known in the prior art; trialkylamine oxides, as also disclosed in TOKAI ELECTRO-CHEMICAL CO.; N-hydroxymorpholine, used in conjunction with N,N-dialkylhydroxylamines, as disclosed in WHITON et al., U.S. Pat. No. 3,265,752, or in conjunction with N-hydroxypiperidine, as disclosed in McCOY et al., U.S. Pat. No. 3,265,751; adducts of phenols and hydroxylamines, as disclosed in ALBERT et al., U.S. Pat. No. 3,493,063; reaction products of nitrous acid and 1,3-dichlorobutene-2 or diisobutylene, as disclosed in BENJAMINS, U.S. Pat. No. 3,560,577, which also refers to nitrogen dioxide, the addition product of 1,3-dichloro-2-butene and nitrogen dioxide, and ion-exchange resin containing nitrite ions, as being known in the prior art; butyraldoxime, as disclosed in KEOWN, U.S. Pat. No. 2,947,795; and nitrogen tetroxide-diisobutylene addition products, as disclosed in COLBERT, U.S. Pat. No. 3,175,012.

Further, sulfur-containing compounds, and even, specifically, hydrogen sulfide and certain mercaptans, are known as popcorn polymer inhibitors. HASKELL, U.S. Pat. No. 4,404,413, not only discloses elemental phosphorous and carbon disulfide, and additionally mentions ethyl disulfide as being known in the prior art, but, yet further, refers to hydrogen sulfide, and to ethane-, propane-, and hexane-thiol, also as being known for inhibiting popcorn polymer growth.

However, the HASKELL patent provides only limited discussion with respect to this matter. Various aspects of using hydrogen sulfide and mercaptans for inhibiting popcorn polymer growth are neither disclosed nor suggested in the prior art.

For instance, the only mercaptans discussed in HASKELL for inhibiting popcorn polymer formation are specific alkyl monothiols. There is no mention of alkyl monothiols in general, or of other types of aliphatic mercaptans, such as alkyl dithiols; particularly, there is no disclosure or suggestion of aromatic mercaptans in any form.

There is further no disclosure or suggestion, for any mercaptan, including those specific mercaptans listed in HASKELL, that popcorn polymer inhibition could be especially effective where the mercaptan inhibitor and the organic materials are similar with respect to structure or particular properties. As specific examples, there is no indication that such superior results are possible where both the mercaptan and the organic material are aromatic compounds, or where the mercaptan and the organic material have not only similar boiling points, but also vapor pressures which become similar as their respective boiling points are reached.

Also, not disclosed or suggested, for any mercaptan, or for hydrogen sulfide, are particular different methods of using such compounds as inhibitors. As an example, there is no mention of either continuously or intermittently adding the inhibitor to popcorn polymer-forming material. There is further no reference to treating actual popcorn polymer already formed, i.e., applying the inhibitor to the popcorn polymer itself, to prevent or retard further growth thereof.

It has been discovered that such uses of mercaptans and hydrogen sulfide, not previously disclosed or suggested, will inhibit popcorn polymer growth. It is further considered that, among the indicated newly discovered applications of mercaptans and hydrogen sulfide, use of particular such sulfur-containing compounds with particular organic materials, or popcorn polymers derived therefrom, and use of particular types of such sulfur-containing compounds with particular types of organic materials, or with popcorn polymers derived therefrom, will provide particularly effective results with respect to inhibiting growth (or further growth) of popcorn polymer.

SUMMARY OF THE INVENTION

The invention pertains to particular uses of sulfur-containing compounds, especially mercaptans, and hydrogen sulfide, for inhibiting popcorn polymer growth. Preferably, in the various embodiments of the invention, the amount of such sulfur-containing compound used is sufficient to inhibit popcorn polymer growth.

In one embodiment of the process of the invention, organic material from which popcorn polymer is formed is treated with at least one sulfur-containing compound selected from the group consisting of mercaptans and hydrogen sulfide; this embodiment of the invention is particularly suitable where the organic material is provided as a moving stream. In this embodiment, such at least one sulfur-containing compound is added to the organic material, either continuously or intermittently.

Further with regard to this embodiment, the preferred concentration of inhibitor, added to the organic material, is 0.5–100,000 wppm. More preferably, the concentration is 5–1,000 wppm.

The invention further pertains to treatment of popcorn polymer-forming organic material, with at least one mercaptan selected from the group consisting of aromatic mercaptans and aliphatic dithiols. Preferably, the at least one mercaptan comprises at least one aromatic mercaptan, and the organic material comprises at least one aromatic monomer.

Also within the scope of the invention, and also being preferred, is treatment of popcorn polymer-forming material with at least one mercaptan, wherein the organic material and the at least one mercaptan are characterized both by similar boiling points, and by vapor pressures which become similar as their respective boiling points are reached. Included among the organic material/mercaptan combinations which meet these two criteria are 1,3-butadiene/methyl mercaptan, isoprene/ethyl mercaptan, and styrene/thiophenol.

The invention yet additionally pertains to inhibiting popcorn-polymer growth, in a system for organic material from which popcorn polymer is formed. Specifically, such inhibition of popcorn polymer growth in the system is effected by addition, to the system, of at least one mercaptan selected from the group consisting of aromatic mercaptans and aliphatic dithiols.

In another embodiment of the process of the invention popcorn polymer is treated, to inhibit the growth thereof; such treatment is effected with at least one sulfur-containing compound selected from the group consisting of mercaptans and hydrogen sulfide. Preferably, the treatment is conducted in the absence, or at least the substantial absence, or essential absence, of organic material from which the popcorn polymer is formed.

The preferred temperature range for conducting this popcorn polymer treatment is 20°–100° C. Also as preferred parameter ranges, the vapor pressure of the at least one mercaptan is between 0.1–3.0 atmospheres during the treatment, and the treatment is conducted for a period of 15 minutes–100 hours.

DESCRIPTION OF PREFERRED EMBODIMENTS

The inhibitor compositions of the invention are hydrogen sulfide, and those mercaptans which inhibit popcorn polymer formation in or from organic material, and/or inhibit the further growth of extant popcorn polymer seeds or sources, when employed in the process of the invention, as described herein. Within the scope of the invention is treatment of any organic material in which, or from which, popcorn polymer forms, as well as treatment of any popcorn polymer seeds or sources formed from such organic material, when such treatment is performed in accordance with the invention, also as set forth herein.

As used herein, the term "mercaptan" is understood to refer generally to the sulfur analogs of alcohol, including both the aliphatic mercaptans and the aromatic mercaptans. The term is further understood to encompass both the substituted and nonsubstituted such aliphatic and aromatic mercaptans, as well as mercaptans with one —SH group, or multiple —SH groups.

The aromatic mercaptans include those with only one benzene ring, as well as those of two or more benzene rings, e.g., the naphthalenes Particular suitable aromatic mercaptans include the thiophenols, e.g., thiophenol itself, the thiocresols, e.g., m-thiocresol and p-thiocresol, the benzylmercaptans, e.g., benzylmercaptan, 2-chlorobenzylmercaptan, and 4-chlorobenzylmercaptan, the naphthalenethiols, e.g., 1-naphthalenethiol and 2-naphthalenethiol, 3,4-dimercaptotoluene, and 4-methoxy-alphatoluenethiol.

Particular suitable aliphatic mercaptans with one —SH group include methyl mercaptan and ethyl mercaptan. Particular suitable aliphatic mercaptans with more than one —SH group include 1,2-ethanedithiol, 2,3-butanedithiol, 1,4-butanedithiol, and 1,3-propanedithiol.

The mercaptan inhibitors of the invention are advantageous in being relatively inexpensive. As a further benefit, they are available from a variety of sources.

Also as used herein, the term "organic material" is understood as encompassing all organic material wherein, or from which, popcorn polymer forms. Such organic material includes, but is not limited to, olefins and diolefins, particularly the conjugated diolefins, as well as the vinyl compounds, as discussed in HASKELL, U.S. Pat. No. 4,404,413; this patent is incorporated herein in its entirety, by reference thereto.

Specifically, suitable such organic material includes monovinyl compounds such as styrene, acrylic acid and its esters, such as methyl acrylate, ethyl acrylate, and butyl acrylate; methacrylates such as methyl methacrylate, ketones such as methyl vinyl ketone, and nitriles such as acrylonitrile. Appropriate divinyl compounds include 1,3-butadiene, isoprene, dimethyl-2,3-buta-1,3-diene,chloroprene, and bromoprene.

Further as to the organic material, two or more monomers, such as any combination of those discussed above, as well as popcorn polymer sources or seeds formed from any such combination, may also be treated with the inhibitor of the invention.

Various additional terms, as used herein, are understood to have particular means. These are set forth below.

While retaining its ordinary meaning in the art, i.e., as the starting unit for polymerization, the term "monomer" encompasses all organic material suitable for treatment with the compounds of the invention. It further encompasses all such organic material wherein are formed the popcorn polymer seeds and sources susceptible to such treatment.

The term "inhibit" refers to all degrees of adversely affecting the formulation of popcorn polymer. Completely halting popcorn polymer growth is included as well as slowing such growth.

The term "treatment" encompasses any use of one or more of the sulfur-containing compound inhibitors of the invention, for inhibiting popcorn polymer formation. Such treatment includes contacting monomer with inhibitor, by any appropriate means, e.g., with the inhibitor being admixed with monomer, or added thereto; as an advantage for use with monomer in this manner, the inhibitor is effective in both the liquid and the vapor phases.

This treatment also includes effecting the contact by any appropriate means. Preferably, inhibitor is added to the monomer in such a manner as to be dispensed therethrough, and thereby provide optimal protection against popcorn polymer formation.

Yet further, treatment of monomer, with inhibitor of the invention, encompasses contacting monomer, with the inhibitor, in all stages and steps of recovery, manufacture, use, storage, or any other type of handling of the monomer. For instance, included is use of the inhibitor in processes for separating desired monomer from a mixed hydrocarbond stream, and in processes involving chemical reaction of the monomer; also included is addition of the inhibitor to the monomer retained in storage tanks.

Treatment of monomer with inhibitor of the invention can act against popcorn polymer in different ways. Such application can prevent, or at least retard, formation of popcorn polymer in or from the organic material. It can also kill, or at least slow the growth of popcorn polymer with which it comes into contact, e.g., seeds or deposits in the systems wherein monomer is recovered, used, or stored.

Suitable means of effecting the indicated treatment of popcorn polymer-forming organic material include continuous addition of the inhibitor to such monomer; intermittent addition is also appropriate. Both continuous and intermittent addition of the inhibitor are particularly suitable where the monomer is provided as a flowing stream.

The results to be obtained from continuous and intermittent addition of inhibitor are not necessarily the same. Different advantages and disadvantages appear to be attendant upon each such manner of addition.

Continuous addition of inhibitor tends to maintain prevention of seed formation, and is therefore advantageous in combatting any appearance of popcorn polymer. However, it requires that a greater amount of inhibitor be used, and is correspondingly more expensive.

Intermittent addition of inhibitor, involving the addition of discrete portions of inhibitor into the organic material at spaced intervals, will, upon each such admission of the inhibitor, "kill" whatever seeds have formed during the interval between additions, i.e., prevent their further growth, or at least retard such growth. Because such addition is not continuous, it requires less of the inhibitor than is employed in continuous addition, and is correspondingly cheaper; however, it tends to allow the growth of new seeds during periods of time between additions of inhibitor.

In both continuous and intermittent addition, the amount of inhibitor to be used will vary according to different factors, including: how readily popcorn polymer formation occurs in the monomer or monomers being treated; the growth rate of such popcorn polymer once polymerization thereof has been initiated; and, if popcorn polymer formation has already begun, the size and number of seeds present. For instance, whether in liquid or vapor phase, where continuous addition is effected, concentrations of between about 0.5 wppm and about 100,000 wppm of inhibitor in the monomer are suitable, with a more preferred range being between about 5 wppm and about 1000 wppm.

Particularly as to intermittent addition, additional factors to be considered in practicing this aspect of the invention, beside the above-discussed addition rate of inhibitor, include: how long each addition should be maintained (i.e., how much inhibitor should be included in each discrete amount added to the monomer); how much time should elapse between such additions of inhibitor; how many such additions should be employed. All factors pertaining to both continuous and intermittent addition may be readily ascertained and determined by one of ordinary skill in the art, to achieve the desired results pertaining to inhibition of popcorn polymer formation.

It is believed that, where the inhibitor of the invention and the monomer to be treated therewith share a certain feature or features, inhibition of polymer growth in this monomer will be particularly effective. In this context, specific inhibitor compounds are considered to be especially effective when used with specific monomers.

As one example, it is thought that particularly good results will be obtained where both the inhibitor of the invention and the monomer are aromatic (in such instance, of course, the inhibitor being an aromatic mercaptan). One possible reason is that, because both are aromatic, the inhibitor is able to disperse more freely in the similarly structured monomer medium.

What is considered to be a more significant reason, also based upon the shared aromaticity, pertains to the previously discussed mechanism for popcorn polymerization. Just as popcorn polymer is thought to form "from the inside out", it is believed that, where inhibitor and monomer are both aromatic, such similarity in structure will allow the inhibitor greater access to the polymerization source to combat growth.

In this respect, a particular advantage would be obtained where a popcorn seed or source has already formed in the monomer, i.e., the inhibitor would be more diffusible into the seed or source. Such greater diffusibility of the inhibitor into the popcorn polymer would render treatment thereof more effective.

A second instance, wherein it is believed that inhibition of popcorn polymer growth will be more effective, is where two conditions are met, i.e., where the boiling points of the inhibitor and monomer are similar, and where their vapor pressures become similar as their boiling points are reached.

Under such circumstances, the inhibitor will distribute evenly through the monomer in both the vapor and the liquid phases, and will remain with the monomer during all stages of processing, storage and handling. For instance, if a hydrocarbon stream incorporating the monomer is subjected to distillation, the inhibitor will remain with the monomer during the separation process, whether the monomer is removed from the other fraction or fractions as distillate or as bottoms.

Methyl mercaptan/1,3 butadiene are considered to be such an advantageous inhibitor/monomer combination. Two more contemplated pairs are ethyl mercaptan/isoprene, and thiophenol/styrene.

Besides being used to treat popcorn polymer-forming monomer, the inhibitors of the invention can be employed to inhibit popcorn polymer growth in yet another manner. Specifically, these inhibitors can be used to treat the actual popcorn polymer seeds and sources—preferably, in the absence, or substantial absence, of monomer.

The effect derived from such treatment of extant popcorn polymer per se is that which is sought with respect to seeds present in monomer which is contacted with the inhibitor. Specifically, the purpose is (as previously discussed with respect to seeds forming between intermittent additions of inhibitor to monomer) to "kill" the popcorn polymer thusly exposed to the inhibitor, i.e., prevent its further growth, or at least to retard such growth.

Like intermittent addition of inhibitor to the monomer, such treatment will lower costs, i.e., by eliminating the need for continuous addition of inhibitor. However, also like intermittent addition, it allows the growth of seeds between treatments.

Specifically, these seeds or sources can be exposed to inhibitor in a system before the admission of monomer thereto, or after its removal therefrom. This treatment is accomplished by any suitable method, such as flushing the system with inhibitor.

The inhibitor thusly used may be in the liquid or the vapor phase. As most broadly construed, the pressure employed in its application is a function of the capacity of the system thusly treated, i.e., the pressure may be as high as such equipment will stand.

More generally, suitable values for the relevant parameters, e.g., pressure, temperature, and exposure time (of the system to inhibitor) will vary according to a multiplicity of factors, including the identity of the popcorn polymer and inhibitor. Such values are readily ascertainable to one of ordinary skill in the art.

For example, a preferred temperature range is between about 20° C. and about 100° C. Vapor pressure of the inhibitor preferably varies anywhere from about 0.0005 atmospheres to about several atmospheres; more preferably, from about 0.1 atmospheres to about 3 atmospheres. Exposure time preferably varies from about 1 minute to several weeks; more preferably, from about 15 minutes to about 100 hours.

In whatever manner they are used, a particular advantage of the inhibitors of the invention is their susceptibility to easy removal from the organic material and/or system with which they have been used; any one of various conventional techniques is suitable. For instance, a commonly used base, such as sodium hydroxide, may be employed for this purpose.

Just as particularly good results are expected where the inhibitor of the invention and the monomer are both aromatic; it is similarly thought that, for treatment of popcorn polymer itself, inhibition of growth will also be enhanced where the inhibitor, and the monomer from which the popcorn polymer is formed, likewise share aromaticity. The reason would be the second and more significant of the two reasons given with respect to treatment of monomer—i.e., the greater diffusibility of inhibitor into the extant popcorn polymer because of similar aromatic structure; in fact, such greater diffusibility would be considered even more important in dealing with the actual popcorn polymer, than with the monomer from which it is formed.

The following experimental procedures demonstrate the utility of the mercaptan and hydrogen sulfide inhibitors of the invention for inhibiting popcorn polymer formation. These procedures are included, not as limiting the invention presented herein, but rather, to be illustrative thereof.

EXPERIMENTAL PROCEDURE I

This first experimental procedure involved exposure of popcorn polymer seeds, derived from different monomers, to different mercaptan inhibitors of the invention; with each seed, such exposure was conducted in the presence of the monomer from which the seed was formed. For the purpose of comparison, also included were controls, i.e., seeds in the presence of their corresponding monomer, but without inhibitor.

Specifically, in each instance, all air was removed from a glass polymerization vessel, either by evacuation, or by flushing with nitrogen. Monomer was then condensed into the vessel at −78° C., or added thereto by syringe, depending upon whether it is liquid or gaseous at room temperature, and upon atmospheric pressure. Specifically, the butadiene was added by the condensation procedure; isoprene and styrene, by syringe.

Where inhibitor was used, a particular proportion thereof, calculated according to the amount of monomer used, was added to the vessel; as to the mode of addition, the inhibitor was added in the same manner and according to the same considerations as the monomer. Specifically, methyl mercaptan was added by condensation; thiophenol and ethyl mercaptan, by syringe. As previously indicated, no inhibitor was used for controls.

A popcorn polymer seed (formed, as stated, from the same monomer providing the environment in the vessel) was placed on the bottom of the vessel for those tests utilizing liquid phase polymerization (i.e., maintaining the seed in the liquid phase). For tests utilizing gas phase polymerization (i.e., maintaining the seed in the gas phase), the seed was suspended in the vessel, so as not to be in contact with liquid therein.

In each test, the system thus established was maintained at 60° C., as a static system, and at autogenic pressure. Popcorn polymer growth rates were measured according to the growth rate of the 1,3-butadiene control.

Specifically, the amount of growth obtained from the butadiene control was arbitrarily designated as 1.0. Growth of all the other seeds was measured according to this standard.

The results of this procedure are set forth in Table I.

TABLE I

| Monomer | Inhibitor/ Conc. (wt. %) | Popcorn Polymer Seed Medium | Treatment Period (Days) | Growth Rate |
| --- | --- | --- | --- | --- |
| butadiene | Control (no inhibitor) | (V) | 14 | 1.0 |
| butadiene | PhSH/0.2 | (V) | 120 | 0 |
| butadiene | MeSH/0.1 | (V) | 45 | 0 |
| isoprene | Control (no inhibitor) | (L) | 14 | 3.0 |
| isoprene | EtSH/0.1 | (L) | 45 | 0 |

EtSH - ethyl mercaptan
MeSH - methyl mercaptan
PhSH - thiophenol
(V) - seeds in vapor phase
(L) - seeds in liquid phase In each instance where mercaptan inhibitor of the invention was present, no polymer growth occurred, whether the seed was maintained in the vapor or liquid phase. In contrast, the popcorn polymer seed exhibited measurable growth over the indicated period, whenever the inhibitor was not used.

EXPERIMENTAL PROCEDURE II

This second experimental procedure involved initially exposing popcorn polymer seeds to mercaptan or hydrogen sulfide inhibitors of the invention, then leaving the seeds in the presence of their corresponding monomers, without inhibitor. As with Experimental Procedure I, controls were also employed, i.e., seeds not subjected to such prior treatment with inhibitor.

In each test according to this procedure utilizing pretreatment with inhibitor, the seed was placed in a glass chamber, after removal of all air therefrom. Inhibitor was then introduced as a gas, at a specified partial pressure, as measured by a pressure gauge; the seed was thus pretreated at 25° C. with the inhibitor for a specified period of time, after which pretreatment, the chamber was again evacuated, this time to remove all inhibitor.

The inhibitor-treated seeds and control seeds were placed in glass polymerization vessels. Monomer was introduced therein, and the tests were otherwise conducted, in the manner set forth in Experimental Procedure I, except that no inhibitor was present during exposure of the seeds to their corresponding monomers. The results are set forth in Table II.

TABLE II

| Monomer | Inhibitor | Inhibitor pressure (psia) | Inhibitor Pretreatment Period (hours) | Popcorn Polymer Seed Medium | Monomer Treatment Period (days) | Popcorn Polymer Growth Rate |
| --- | --- | --- | --- | --- | --- | --- |
| butadiene | Control (no inhibitor) | — | | (V) | 14 | 1.0 |
| butadiene | MeSH/16 | | 24 | (V) | 95 | 0 |
| butadiene | MeSH/16 | | 24 | (L) | 95 | 0 |
| butadiene | EtSH/2 | | 24 | (V) | 60 | 0 |
| butadiene | EtSH/2 | | 24 | (L) | 60 | 0 |
| butadiene | H2S/2 | | 48 | (V) | 30 | 0.3 |
| isoprene | Control (no inhibitor) | — | | (L) | 14 | 3.0 |
| isoprene | MeSH/16 | | 24 | (V) | 95 | 0 |
| isoprene | MeSH/16 | | 24 | (L) | 95 | 0 |

EtSH - ethyl mercaptan
MeSH - methyl mercaptan
(V) - seeds in vapor phase
(L) - seeds in liquid phase In each instance of pretreatment with a mercaptan inhibitor of the invention, the popcorn polymer seed experienced no growth from subsequent exposure to monomer; where the inhibitor of the invention was hydrogen sulfide, growth did occur, but at a significantly lower rate than that of the seeds not thusly pretreated. Such lack of growth, and lower growth rate, occurred even though no inhibitor was present during such exposure.

Finally, although the invention has, as been noted above, been described with reference to particular means, materials and embodiments, it should be noted that the invention is not limited to the particulars disclosed, and extends to all equivalents within the scope of the claims.

What is claimed is:

1. A method for inhibiting popcorn polymer growth in organic material, comprising adding intermittently, to said organic material, at least one sulfur containing compound selected from the group consisting of mercaptans and hydrogen sulfide.

2. The method of claim 1, wherein said at least one sulfur-containing compound is provided in a concentration of from about 0.5 to about 100,000 wppm of said organic material.

3. The method of claim 2, wherein said at least one sulfur-containing compound is provided in a concentration of from about 5 to about 1000 wppm of said organic material.

4. A method for inhibiting popcorn polymer growth, in organic material comprising at least one aromatic monomer, said method comprising treating said organic material with at least one aromatic mercaptan.

5. A method for inhibiting the growth of popcorn polymer, comprising treating said popcorn polymer with at least one sulfur-containing compound, said at least one sulfur-containing compound being in the vapor phase, selected from the group consisting of mercaptans and hydrogen sulfide.

6. The method of claim 5, wherein said treatment is conducted in the substantial absence of organic material from which said popcorn polymer is formed.

7. The method of claim 6, wherein said treatment is conducted at a temperature of between about 20° C. and about 100° C. and for a period of between about 15 minutes and about 100 hours, and wherein the vapor pressure of said at least one mercaptan is between about 0.1 atmospheres and about 3.0 atmospheres.

8. The method of claim 6, wherein said at least one sulfur-containing compound comprises at least one mercaptan.

9. The method of claim 8, wherein said at least one mercaptan is selected from the group consisting of methyl mercaptan and ethyl mercaptan, and wherein said organic material, from which said popcorn polymer is formed, is selected from the group consisting of 1,3-butadiene and isoprene.

10. A method for inhibiting the growth of popcorn polymer, formed from organic material comprising at least one aromatic monomer, said method comprising treating said popcorn polymer with at least one aromatic mercaptan.

11. The method of claim 10, wherein said at least one aromatic mercaptan comprises thiophenol, and wherein said at least one aromatic monomer comprises styrene.

12. The method of claim 10, wherein said treatment is conducted in the substantial absence of organic material from which said popcorn polymer is formed.

13. A method for inhibiting popcorn polymer growth in organic material, comprising treating said organic material with at least one mercaptan, in a concentration of from about 5 to about 1000 wppm of said organic material.

14. A method for inhibiting popcorn polymer growth in organic material, comprising treating said organic material with at least one mercaptan, wherein said organic material 1,3-butadiene and said mercaptan is methyl mercaptan.

15. A method for inhibiting popcorn polymer growth in organic material, comprising treating said organic material with at least one mercaptan, wherein said organic material is isoprene and said mercaptan is ethyl mercaptan.

16. A method for inhibiting popcorn polymer growth in organic material, comprising treating said organic material with at least one mercaptan, wherein said organic material is styrene and said mercaptan is thiophenol.

* * * * *